US00PP30203P3

(12) United States Plant Patent
Holtmaat

(10) Patent No.: US PP30,203 P3
(45) Date of Patent: Feb. 12, 2019

(54) ***ECHINACEA* PLANT NAMED 'BLUS302'**

(50) Latin Name: *Echinacea hybrida*
Varietal Denomination: BLUS302

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/731,578

(22) Filed: Jul. 3, 2017

(65) Prior Publication Data

US 2019/0008082 P1 Jan. 3, 2019

(51) Int. Cl.
*A01H 5/02* (2018.01)

(52) U.S. Cl.
USPC ..... Plt./428

(58) Field of Classification Search
USPC ..... Plt./428
CPC . A01H 5/025; A01H 5/02; A01H 5/00; A01H 6/14
See application file for complete search history.

(56) References Cited

PUBLICATIONS

Issuu. Plants Nouveau 2016 Catalog Supplement, published May 10, 2017, retrieved on May 10, 2018, retrieved from the Internet at https://issuu.com/angelatreadwell-palmer/docs/magazine0616, pp. 1-3,5. (Year: 2017).*

* cited by examiner

*Primary Examiner* — June Hwu
(74) *Attorney, Agent, or Firm* — C. A. Whealy

(57) ABSTRACT

A new and distinct cultivar of *Echinacea* plant named 'Blus302', characterized by its broadly upright plant habit; moderately vigorous growth habit; freely branching habit; strong flowering stems; numerous large single-type inflorescences with light orange and red purple-colored ray florets and orange red-colored receptacle spines; and good garden performance.

2 Drawing Sheets

Botanical designation: *Echinacea hybrida*.
Cultivar denomination: 'BLUS302'.

BACKGROUND OF THE INVENTION

The present invention relates to a new and distinct cultivar of *Echinacea* plant, botanically known as *Echinacea hybrida*, and hereinafter referred to by the name 'Blus302'.

The new *Echinacea* plant is a product of a planned breeding program conducted by the Inventor in Zuidwolde, The Netherlands. The objective of the breeding program is to develop new freely branching and relatively compact *Echinacea* plants with unique and attractive ray floret coloration.

The new *Echinacea* plant originated from an open-pollination in July, 2014 in Zuidwolde, The Netherlands of *Echinacea hybrida* 'Cleopatra', disclosed in U.S. Plant Pat. No. 24,631, as the female, or seed, parent with an unknown selection of *Echinacea hybrida* as the male, or pollen, parent. The new *Echinacea* plant was discovered and selected by the Inventor as a single flowering plant from within the progeny of the stated open-pollination grown in a controlled greenhouse environment in Zuidwolde, The Netherlands in July, 2015.

Asexual reproduction of the new *Echinacea* plant by in vitro meristem culture in a controlled environment in Zuidwolde, The Netherlands since June, 2016 has shown that the unique features of this new *Echinacea* plant are stable and reproduced true to type in successive generations.

SUMMARY OF THE INVENTION

Plants of the new *Echinacea* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Blus302'. These characteristics in combination distinguish 'Blus302' as a new and distinct *Echinacea* plant:

1. Broadly upright plant habit.
2. Moderately vigorous growth habit.
3. Freely branching habit.
4. Strong flowering stems.
5. Numerous large single-type inflorescences with light orange and red purple-colored ray florets and orange red-colored receptacle spines.
6. Good garden performance.

Plants of the new *Echinacea* can be compared to plants of the female parent, 'Cleopatra'. Plants of the new *Echinacea* differ primarily from plants of 'Cleopatra' in the following characteristics:

1. Flowering stems of plants of the new *Echinacea* are longer and stronger than flowering stems of plants of 'Cleopatra'.
2. Plants of the new *Echinacea* are not as freely branching as plants of 'Cleopatra'.

3. Plants of the new *Echinacea* and 'Cleopatra' differ in ray floret color as ray florets of plants of 'Cleopatra' are yellow in color.

Plants of the new *Echinacea* can be compared to plants of *Echinacea hybrida* 'Purple Emperor', disclosed in U.S. Plant Pat. No. 24,459. In side-by-side comparisons, plants of the new *Echinacea* differ primarily from plants of 'Purple Emperor' in the following characteristics:

1. Flowering stems of plants of the new *Echinacea* are stronger than flowering stems of plants of 'Purple Emperor'.
2. Plants of the new *Echinacea* and 'Purple Emperor' differ in ray floret color as ray florets of plants of 'Purple Emperor' are purple in color.

BRIEF DESCRIPTION OF THE PHOTOGRAPHS

The accompanying photographs illustrate the overall appearance of the new *Echinacea* plant showing the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet is a side perspective view of a typical flowering plant of 'Blus302' grown in a ground bed in an outdoor nursery and placed in a container for the photograph.

The photographs on the second sheet are close-up views of a typical inflorescence (upper photograph) and the upper surface of a typical leaf (lower photograph) of 'Blus302'.

DETAILED BOTANICAL DESCRIPTION

The aforementioned photographs and following observations and measurements describe plants grown during the summer in ground beds in an outdoor nursery in Zuidwolde, The Netherlands and under cultural practices typically used in commercial *Echinacea* production. During the production of the plants, day temperatures ranged from 18° C. to 30° C. and night temperatures ranged from 6° C. to 18° C. Plants were six months old when the photographs and description were taken. In the following description, color references are made to The Royal Horticultural Society Colour Chart, 2015 Edition, except where general terms of ordinary dictionary significance are used.

Botanical classification: *Echinacea hybrida* 'Blus302'.

Parentage:

*Female parent.*—*Echinacea hybrida* 'Cleopatra', disclosed in U.S. Plant Pat. No. 24,631.

*Male parent.*—Unknown selection of *Echinacea hybrida*, not patented.

Propagation:

*Type.*—By in vitro meristem culture.

*Time to initiate roots, summer.*—About one week at temperatures about 25° C.

*Time to produce a rooted young plant, summer.*—About five weeks at temperatures about 21° C.

*Root description.*—Fine, fibrous; typically pale cream in color, actual color of the roots is dependent on substrate composition, water quality, fertilizer type and formulation, substrate temperature and physiological age of roots.

*Rooting habit.*—Freely branching; dense.

Plant description:

*Plant form and growth habit.*—Herbaceous perennial; broadly upright plant habit, narrow inverted triangle; freely branching habit with about seven lateral branches developing per primary branch; moderately vigorous growth habit; moderate growth rate.

*Plant height, soil level to top of foliar plane.*—About 51.6 cm.

*Plant height, soil level to top of floral plane.*—About 64 cm.

*Plant diameter or spread.*—About 35.1 cm.

*Lateral branches.*—Length: About 22.4 cm. Diameter: About 8 mm. Internode length: About 2.6 cm. Aspect: About 30° from vertical. Strength: Moderately strong. Texture and luster: Sparsely pubescent; glossy. Color: Close to 144A.

Leaf description:

*Basal leaves.*—Arrangement: Alternate, simple. Length: About 19.7 cm. Width: About 4.6 cm. Shape: Narrowly ovate to narrowly elliptic. Apex: Acute. Base: Attenuate. Margin: Entire. Texture and luster, upper surface: Sparsely pubescent, strigose, rough, slightly rugose; slightly glossy. Texture and luster, lower surface: Moderately pubescent, strigose, rough; slightly glossy. Venation pattern: Pinnate. Color: Developing leaves, upper surface: Close to 143A. Developing leaves, lower surface: Close to 146B. Fully expanded leaves, upper surface: Close to between NN137A and 147A; venation, close to 143A. Fully expanded leaves, lower surface: Close to NN137C; venation, close to 144D. Petioles, basal leaves: Length: About 4.5 cm. Width: About 3.5 mm. Height: About 3 mm. Strength: Strong, flexible. Texture and luster, upper and lower surfaces: Smooth, glabrous; glossy. Color, upper surface: Close to 144A to 144B. Color, lower surface: Close to 144B.

*Cauline leaves.*—Arrangement: Alternate, simple. Length: About 9.2 cm. Width: About 2.4 cm. Shape: Narrowly ovate to narrowly elliptic. Apex: Acute. Base: Attenuate. Margin: Entire. Texture and luster, upper surface: Sparsely pubescent, strigose; slightly glossy. Texture and luster, upper surface: Moderately pubescent, strigose; slightly glossy. Venation pattern: Pinnate. Color: Developing leaves, upper surface: Close to 143A. Developing leaves, lower surface: Close to 146B. Fully expanded leaves, upper surface: Close to between NN137A and 147A; venation, close to 143A. Fully expanded leaves, lower surface: Close to NN137C; venation, close to 144D. Petioles, cauline leaves: Length: About 1 cm. Width: About 1.5 mm. Height: About 2 mm. Strength: Strong, flexible. Texture and luster, upper and lower surfaces: Smooth, glabrous; glossy. Color, upper surface: Close to 144A to 144B. Color, lower surface: Close to 144B.

Inflorescence description:

*Appearance.*—Large single-type inflorescences with ray and disc florets arranged on a capitulum; inflorescences positioned upright above the foliar plane on strong peduncles.

*Flowering habit.*—Freely flowering habit with about 42 inflorescences developing per plant during the flowering season.

*Fragrance.*—None detected.

*Time to flower*.—Plants begin flowering about 100 days after planting; in the garden, plants flower continuously during the summer in The Netherlands.

*Inflorescence longevity*.—Inflorescences maintain good substance for about two weeks on the plant; inflorescences not persistent.

*Inflorescence buds*.—Height: About 2.8 cm. Diameter: About 4 cm. Shape: Flattened globular. Texture and luster: Smooth, glabrous; matte. Color: Involucral bracts, close to 146A; developing ray florets, close to 151B.

*Inflorescence size*.—Diameter: About 10.8 cm. Depth (height): About 3.8 cm. Disc diameter: About 5.1 cm.

*Receptacles*.—Height: About 1.1 cm. Diameter: About 1.5 cm. Color: Close to 155A.

*Ray florets*.—Quantity and arrangement: About 22 arranged in a single whorl. Length: About 4.9 cm. Width: About 1 cm. Shape; Oblanceolate. Apex: Emarginate; shallowly indented. Base: Cuneate. Margin: Entire. Texture and luster, upper surface: Smooth, glabrous, slightly velvety; matte. Texture and luster, lower surface: Smooth, glabrous, slightly velvety; slightly glossy. Aspect: Mostly horizontal to slightly drooping, about 5° below horizontal; straight, not twisting. Color: When opening, upper surface: Close to 26D; towards the base, close to 60D. When opening, lower surface: Close to 16B and 26C; towards the base, close to 53D. Fully opened, upper surface: Close to 26D; towards the base, close to 60D; venation, close to 16B; color does not fade with development. Fully opened, lower surface: Close to 16B and 26C; towards the base, close to 53D; venation, close to 12C; color does not fade with development.

*Disc florets*.—Quantity and arrangement: About 300 per inflorescence, arranged spirally at the center of the receptacle. Length: About 1.1 cm. Diameter: About 3.5 mm. Shape: Tubular; proximally, 15% free, not fused. Apex: Acute. Base: Fused. Margin: Entire. Aspect: Mostly upright. Texture and luster, inner and outer surfaces: Smooth, glabrous; glossy. Color, when opening, inner and outer surfaces: Apex: Close to 176A. Mid-section: Close to 144C. Base: Close to 152D. Color, fully opened, inner and outer surfaces: Apex: Close to 176A. Mid-section: Close to 144C. Base: Close to 152D.

*Receptacle spines*.—Quantity: One per disc floret. Length: About 1.7 cm. Diameter: About 1.5 mm. Shape: Acicular. Apex: Narrowly acute. Base: Cuneate. Texture and luster: Smooth, glabrous; glossy. Color: Apex: Close to 34A to 34B. Mid-section: Close to 144A. Base: Close to 145D.

*Involucral bracts*.—Quantity per inflorescence: About 80 arranged in about four whorls. Length: About 1.3 cm. Width: About 4 mm. Shape: Narrowly ovate. Apex: Acute. Base: Cuneate. Margin: Entire; moderately pubescent. Texture and luster, upper and lower surfaces: Smooth, glabrous; slightly glossy. Color, upper surface: Close to 143B. Color, lower surface: Close to 137C.

*Peduncles*.—Length, terminal peduncle: About 13.7 cm. Diameter, terminal peduncle: About 8 mm. Length, third peduncle: About 8.6 cm. Diameter, third peduncle: About 5 mm. Strength: Strong. Aspect, terminal peduncle: Upright. Aspect, third peduncle: About 30° from vertical. Texture and luster: Sparsely pubescent; moderately glossy. Color: Close to 146A with random spots, close to 144C and 144D.

*Reproductive organs*.—Androecium (present only on disc florets): Quantity per floret: Five. Filament length: About 5 mm. Filament color: Close to 151B. Anther length: About 3 mm. Anther width: About 0.5 mm. Anther shape: Narrowly oblong. Anther color: Close to 203C. Pollen amount: Moderate. Pollen color: Close to 15A. Gynoecium (present only on disc florets): Quantity per floret: One. Pistil length: About 7 mm. Style length: About 5 mm. Style color: Close to 151B. Stigma diameter: About 3.5 mm. Stigma shape: Decurrent, cleft. Stigma color: Close to 200A. Ovary color: Close to 145D. Seeds and fruits: Seed and fruit development have not been observed on plants of the new *Echinacea* to date.

Disease & pest resistance: Plants of the new *Echinacea* have not been shown to be resistant to pathogens and pests common to *Echinacea* plants.

Garden performance: Plants of the new *Echinacea* have exhibited good garden performance and to tolerate rain and wind. Plants of the new *Echinacea* have been observed to tolerate high temperatures of about 35° C. and to be suitable for USDA Hardiness Zones 3 to 10.

It is claimed:

1. A new and distinct *Echinacea* plant named 'Blus302' as illustrated and described.

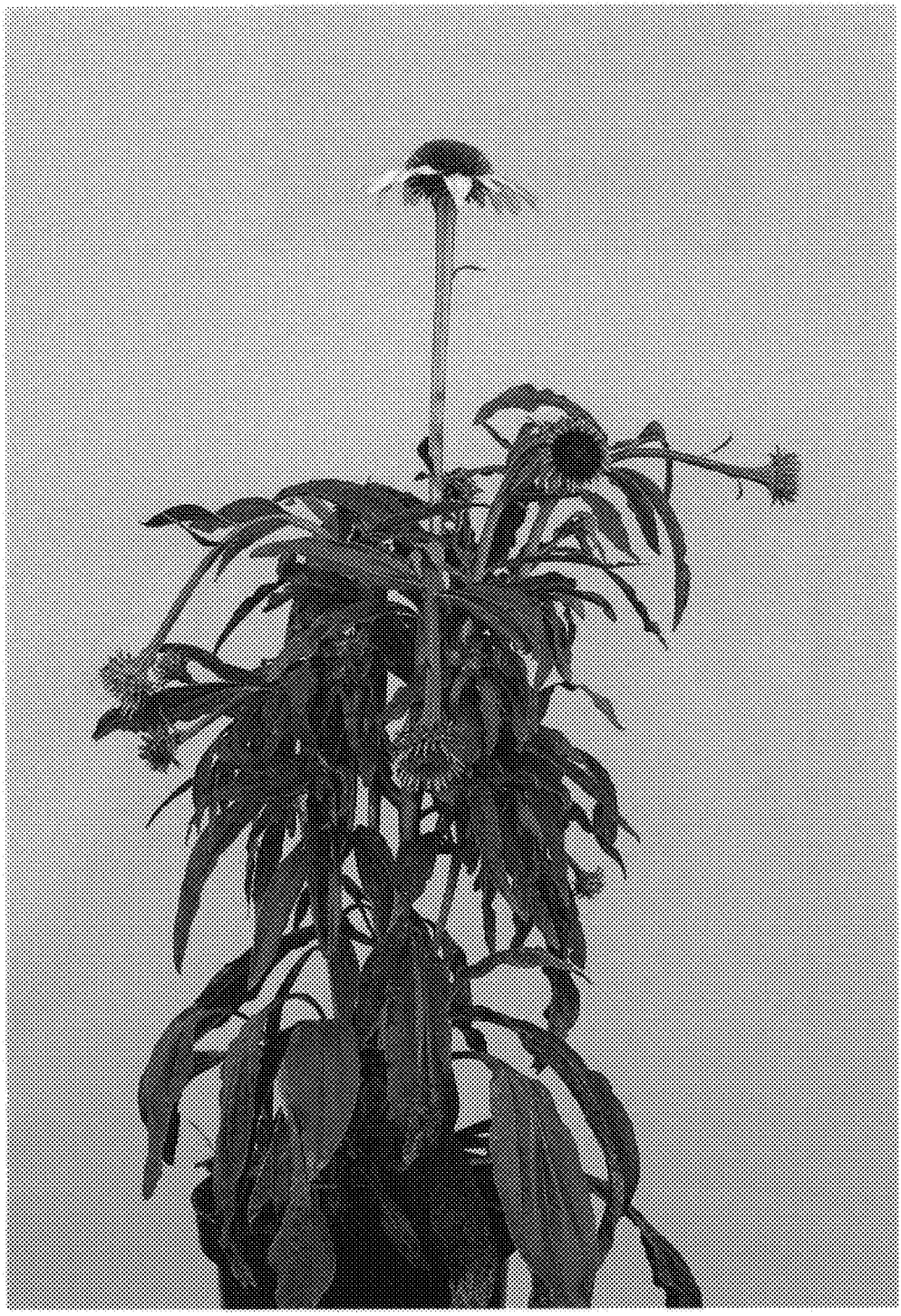

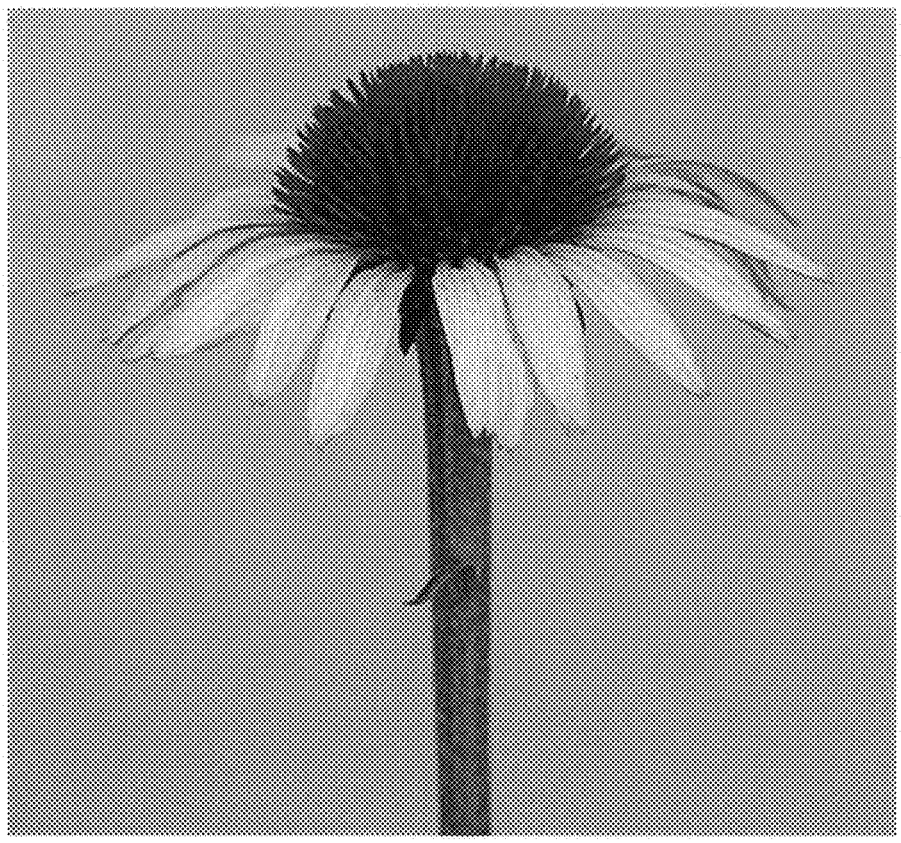
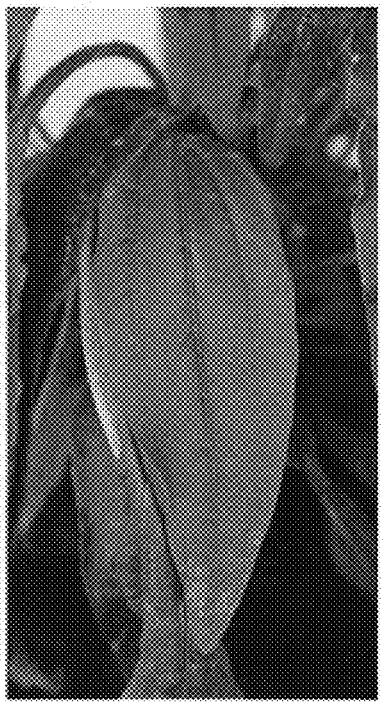

* * * * *